US005154701A

United States Patent [19]
Cheer et al.

[11] Patent Number: 5,154,701
[45] Date of Patent: * Oct. 13, 1992

[54] HEMOSTASIS VALVE

[75] Inventors: John Cheer, Sea Girt; Kevin Powell, Branchburg, both of N.J.

[73] Assignee: Adam Spence Corporation, Wall, N.J.

[*] Notice: The portion of the term of this patent subsequent to Apr. 7, 2009 has been disclaimed.

[21] Appl. No.: 785,995

[22] Filed: Oct. 31, 1991

Related U.S. Application Data

[63] Continuation of Ser. No. 721,821, Jun. 26, 1991.

[51] Int. Cl.$^5$ .............................................. A61M 5/178
[52] U.S. Cl. .................................... 604/167; 604/169; 604/256; 137/849
[58] Field of Search ............... 604/167, 169, 237, 244, 604/256, 278; 137/843, 845, 849; 251/149.1

[56] References Cited

U.S. PATENT DOCUMENTS

| | | | |
|---|---|---|---|
| 3,994,287 | 11/1976 | Turp et al. | 604/167 |
| 4,424,833 | 1/1984 | Spector et al. | 137/849 |
| 4,673,393 | 6/1987 | Suzuki et al. | 604/167 |
| 4,929,235 | 5/1990 | Merry et al. | 604/167 |
| 4,960,412 | 10/1990 | Fink | 604/167 |
| 5,000,745 | 3/1991 | Guest et al. | 604/167 |

Primary Examiner—Cary E. O'Connor
Attorney, Agent, or Firm—Oblon, Spivak, McClelland, Maier & Neustadt

[57] ABSTRACT

The invention is a hemostasis valve having a main body, a proximal end cap, a register member, and a reinforcing member. The main body has a proximal end, a distal end, and a first bore having a proximal end at the proximal end of the main body and a distal end at the distal end of the main body. The first bore has a first flexure-receiving enlargement at its proximal end. The proximal end cap is joined to the proximal end of the main body and forms therewith a valve chamber. The proximal end cap has a second bore formed therethrough that is at least approximately an extension of the first bore. The register member is received in the valve chamber adjacent the proximal end cap. The register member has a proximal portion and a distal portion. The proximal portion of the register member has a third bore formed therethrough that is at least approximately an extension of the first and second bores. The distal portion of the register member is flexible and contains at least one slit on the extension of the first, second, and third bores. The third bore has a second flexure-receiving enlargement adjacent its distal portion. The reinforcing member is received in the valve chamber adjacent the main body, and it has at least one slit on the extension of the first, second, and third bores.

14 Claims, 2 Drawing Sheets

HEMOSTASIS VALVE

This application is a continuation application under 37 C.F.R. 1.60, of copending prior application Ser. No. 07/721,821 (pending), filed on Jun. 26, 1991.

BACKGROUND OF THE INVENTION

1. Field of the Invention

This invention pertains to a hemostasis valve having a bore formed therethrough through which, in use, a catheter is first inserted and then withdrawn. The hemostasis valve is designed to make liquid-tight contact with the catheter while it is in place and while the catheter is being inserted or withdrawn, and it is designed to make a liquid-tight seal of the bore in the absence of the catheter.

2. Background of the Invention

This invention is an improvement on the hemostasis valve shown in U.S. Pat. No. 4,610,665, issued Sep. 09, 1986 to Matsumoto et al., the specification of which is hereby incorporated herein by reference.

The hemostasis valve shown in the Matsumoto et al. patent is used to introduce a catheter into an artery, and it is intended to seal low pressure liquid (i.e., blood) in the artery during insertion and withdrawal of the catheter. However, the internal components of the valve (i.e., the valve seal) are fabricated entirely from soft silicone material. This results in the problem that occasionally the valve seal is dislodged from the valve body when the catheter is inserted into the valve or withdrawn from the valve.

OBJECTS OF THE INVENTION

It is the principal object of this invention to provide a hemostasis valve that mitigates or eliminates the foregoing problem.

It is a specific object of this invention to provide a hemostasis valve that contains a rigid, reinforced, monolithic valve seal the construction of which prevents the valve seal from being dislodged during insertion and withdrawal of the catheter.

It is a still more specific object of the invention to provide a hemostasis valve formed of two different components (a register member and a reinforcing member) that can be fabricated from two different durometer materials, which permits improved performance of the valve in specific applications.

SUMMARY OF THE INVENTION

The invention is a hemostasis valve having a main body, a proximal end cap, a register member, and a reinforcing member. The main body has a proximal end, a distal end, and a first bore having a proximal end at the proximal end of the main body and a distal end at the distal end of the main body. The first bore has a first flexure-receiving enlargement at its proximal end. The proximal end cap is joined to the proximal end of the main body and forms therewith a valve chamber. The proximal end cap has a second bore formed therethrough that is at least approximately an extension of the first bore. The register member is received in the valve chamber adjacent the proximal end cap. The register member has a proximal portion and a distal portion. The proximal portion of the register member has a third bore formed therethrough that is at least approximately an extension of the first and second bores. The distal portion of the register member is flexible and contains at least one slit on the extension of the first, second, and third bores. The third bore has a second flexure-receiving enlargement adjacent its distal portion. The reinforcing member is received in the valve chamber adjacent the main body, and it has at least one slit on the extension of the first, second, and third bores.

DETAILED DESCRIPTION OF THE PRESENTLY PREFERRED EMBODIMENT

Figure 5:
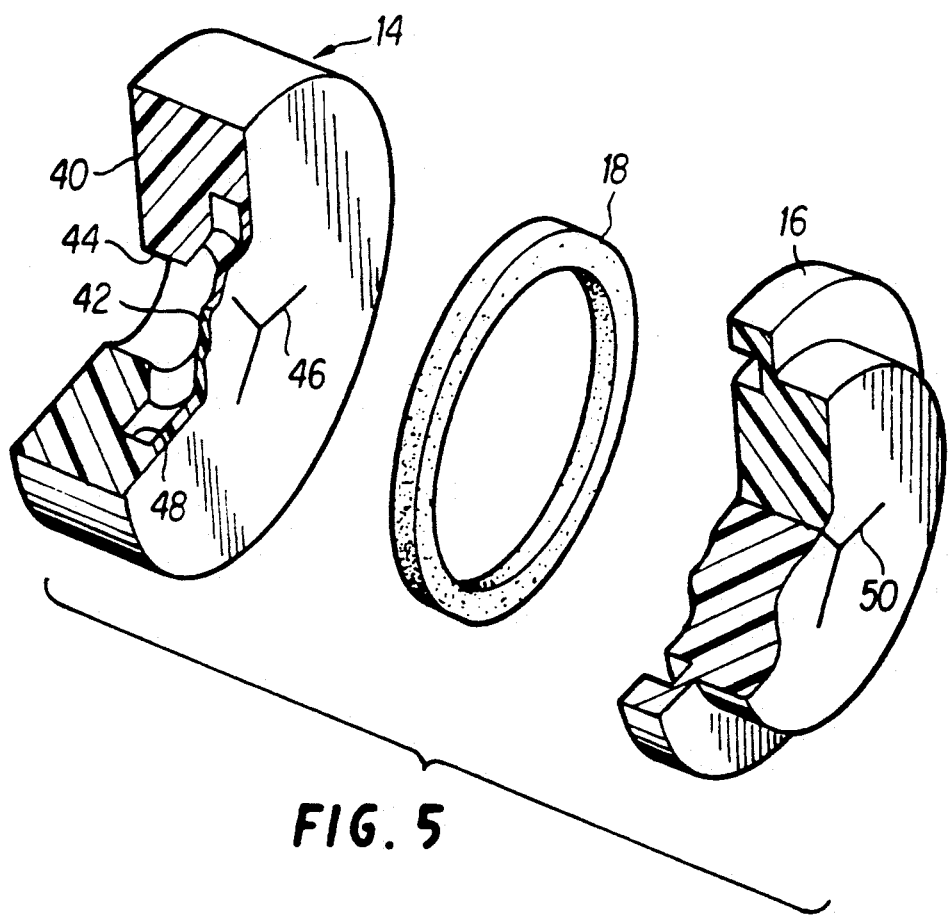
FIG. 5 is an exploded perspective view on an enlarged scale of the components of the valve seal shown in FIG. 3.
Figure 1:
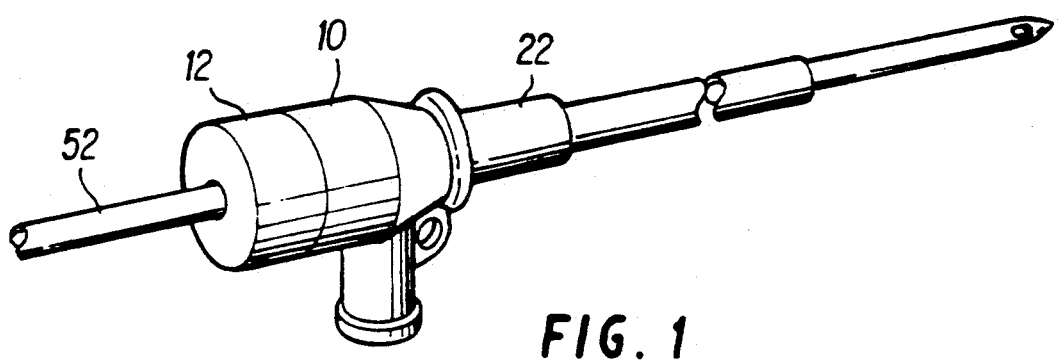
FIG. 1 is a perspective view of the presently preferred embodiment of the invention with a catheter inserted therethrough.
Figure 2:
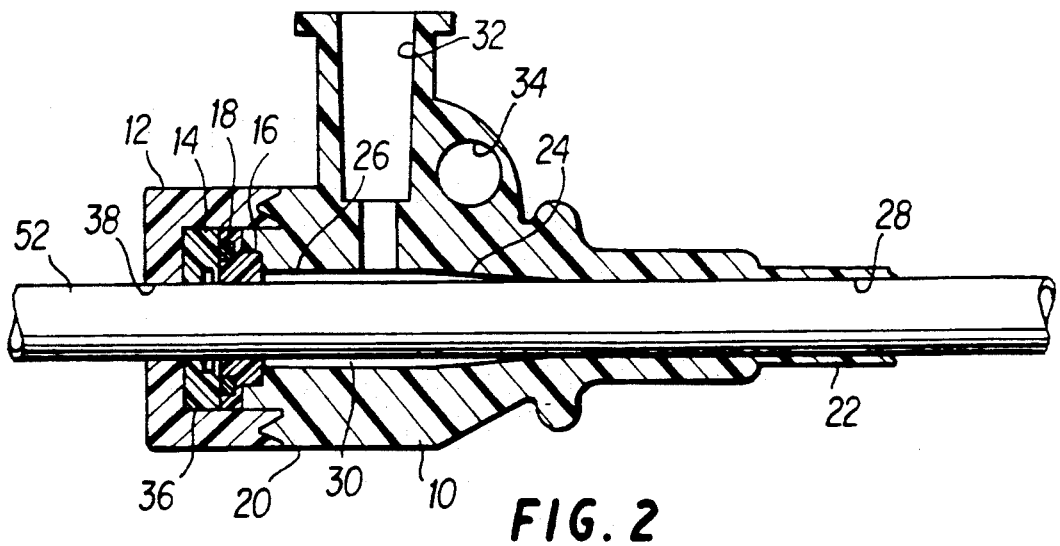
FIG. 2 is a cross-sectional view of the presently preferred embodiment of the invention with a catheter inserted therethrough.
Figure 3:
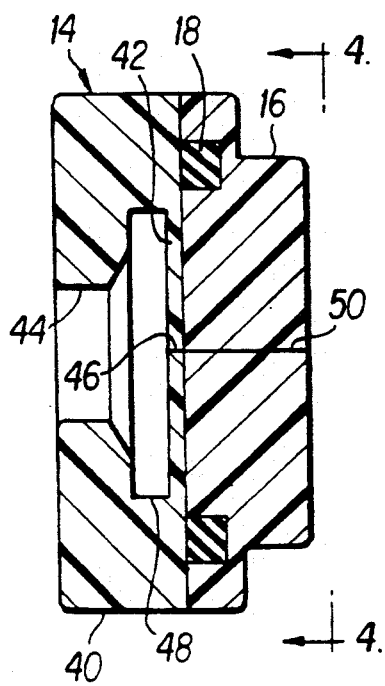
FIG. 3 is a cross-sectional view on an enlarged scale of the valve seal used in the presently preferred embodiment of the invention.
Figure 4:
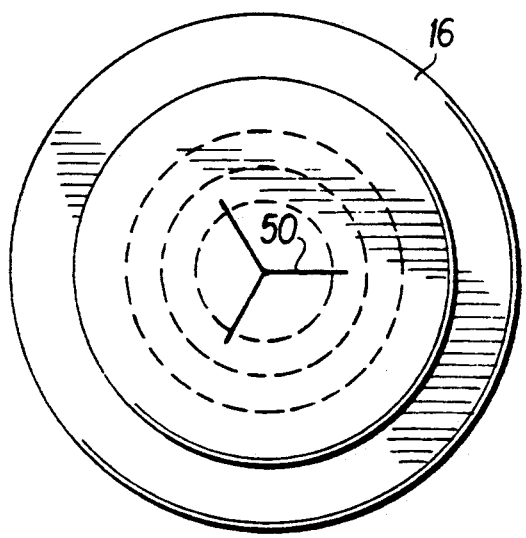
FIG. 4 is an end view of the valve seal shown in FIG. 3 on the line 4—4.

The hemostasis valve shown in the drawings comprises a main body 10, a proximal end cap 12, a register member 14, a reinforcing member 16, and an reinforcing ring 18.

The main body 10 has a proximal end 20 and a distal end 22. A first bore 24 is located in the main body 10 and has a proximal end 26 at the proximal end 20 of the main body 10 and a distal end 28 at the distal end 22 of the main body 10. The first bore 24 has a first flexure-receiving enlargement 30 at its proximal end 26. A fourth bore 32 (the second and third bores are described below in connection with the proximal end cap 12 and the register member 14, respectively) is also located in the main body 10 and extends from a surface of the main body 10 to the first bore 24. A hang-up hole 34 extends through the main body 10, preferably at least approximately perpendicularly to the first bore 24. The main valve body 10 is preferably made from rigid plastic, and it can be very similar to or identical to the corresponding part illustrated in the Matsumoto et al. patent.

The proximal end cap 12 is joined to the proximal end 20 of the main body 10 and forms therewith a valve chamber 36. The proximal end cap 12 has a second bore 38 formed therethrough that is at least approximately an extension of the first bore 24. If the first bore 24 and the second bore 38 are circular in cross-section, as is usually the case, the first bore 24 and the second bore 38 are preferably at least approximately coaxial. The proximal end cap 12 is preferably made from rigid plastic, and it is preferably permanently fixed to the main body 10 after the assembly consisting of the register member 14, the reinforcing member 16, and the reinforcing ring 18 has been inserted into the valve chamber 36. (By "permanently fixed," we mean that the proximal end cap 12 cannot be separated from the main body 10 without damaging one or the other or both of those two components.) As shown, the proximal end cap 12 is preferably cup-shaped to define the valve chamber 36. The proximal end cap 12 can also be very similar to or identical to the corresponding part illustrated in the Matsumoto et al. patent.

The register member 14 is received in the valve chamber 36 adjacent the proximal end cap 12. The register member 14 has a proximal portion 40 and a distal portion 42. The proximal portion 40 of the register member 14 has a third bore 44 formed therethrough that is at least approximately an extension of the first bore 24 and the second bore 38. If the first bore 24 and the second bore 38 are circular in cross-section, as is usually the case, the first bore 24, the second bore 38, and the third bore 44 are preferably at least approximately coaxial. The distal portion 42 of the register member 14 is flexible and contains at least one slit 46 on the extension of the first bore 24, the second bore 38, and the third bore 44. Preferably, and as illustrated, the slit 46 is a tricusp slit. The third bore 44 contains a second flexure-receiving enlargement 48 adjacent the distal portion 42 of the register member 14. Preferably the proximal portion 40 of the register member 14 makes planar abutting contact with the proximal end cap 12 at a surface at least approximately perpendicular to the third bore 44. The register member 14 is preferably made from 35A natural medical grade silicone.

The reinforcing member 16 is received in the valve chamber 36 adjacent the main body 10. It is preferably permanently joined with the register member 14 to form a subassembly. (By "permanently joined," we mean that the register member 14 and the reinforcing member 16 cannot be separated from each other without damaging the one or the other or both of the two components.) The reinforcing member 16 has at least one slit 50 on the extension of the first bore 24, the second bore 38, and the third bore 44. Preferably, and as illustrated, the slit 50 is a tricusp slit. Also preferably the reinforcing member 16 makes planar abutting contact with the register member 14 at a surface at least approximately perpendicular to the third bore 44. The reinforcing member 16 is preferably made from 35A natural medical grade silicone. However, the durometer of the silicone may be changed to a harder or softer durometer for specific applications.

The reinforcing ring 18 is preferably made from nylon. However, it should be noted that the reinforcing ring 18 can be made from materials other than nylon. It is preferably permanently joined with the register member 14 and the reinforcing member 16 to form a subassembly. (By "permanently joined," we mean that the register member 14, the reinforcing member 16, and the reinforcing ring 18 cannot be separated from each other without damaging one or more of the three components.)

The first flexure-receiving enlargement 30 is preferably much longer in the direction of the first bore 24 than is necessary to receive the flexure of the reinforcing member 16. This permits the first flexure-receiving enlargement 30 to serve as a drainage chamber that is drained by the fourth bore 32.

The transverse dimensions of the third bore 44 are preferably smaller than the transverse dimensions of the catheter that is to be passed through the valve. If, as is usually the case, both are circular in cross-section, this means that the diameter of the third bore 44 is preferably less than the diameter of the catheter that is to be passed through it.

In use, when a catheter 52 is inserted through the second bore 38, the third bore 44, the slit 46 in the distal portion 42 of the register member 14, the slit 50 in the reinforcing member 16, and the first bore 24, the reinforcing member 16 flexes into the first flexure-receiving enlargement 30 and makes liquid-tight contact with the catheter 52. When the catheter 52 is later removed through the first bore 24, the slit 50 in the reinforcing member 16, the slit 46 in the distal portion 42 of the register member 14, the third bore 44, and the second bore 38, the reinforcing member 16 and the distal portion 42 of the register member 14 flex into the second flexure receiving enlargement 48 and make liquid-tight contact with the catheter 52. When the catheter 52 is not received in the hemostasis valve, the reinforcing member 16 and the distal portion 42 of the register member 14 provide a liquid-tight seal of the first bore 24.

Caveat

Obviously, numerous modifications and variations of the present invention are possible in light of the above teachings. It is therefore to be understood that, within the scope of the appended claims, the invention may be practiced otherwise than as specifically described herein.

What is claimed is:

1. A hemostasis valve comprising:
   (a) a main body having:
      (i) a proximal end and a distal end and
      (ii) a first bore having a proximal end at the proximal end of said main body and a distal end at the distal end of said main body, said first bore having a first flexure-receiving enlargement at its proximal end;
   (b) a proximal end cap joined to the proximal end of said main body and forming therewith a valve chamber, said proximal end cap having a second bore formed therethrough that is at least approximately an extension of said first bore;
   (c) a register member that is received in said valve chamber adjacent said proximal end cap, said register member having:
      (i) a proximal portion that has a third bore formed therethrough that is at least approximately an extension of said first and second bores;
      (ii) a distal portion; and
      (iii) a second flexure-receiving enlargement of said third bore adjacent said distal portion; and
   (d) a reinforcing member that is received in said valve chamber adjacent said main body, sad reinforcing member having at least one slit on the extension of said first, second, and third bores, whereby:
   (e) when a catheter is inserted through said second bore, said third bore, said at least one slit in said reinforcing member, and said first bore, said reinforcing member flexes into said first flexure-receiving enlargement and makes liquid-tight contact with the catheter;
   (f) when a catheter is removed through said first bore, said at least one slit in said reinforcing member, said third bore, and said second bore, said reinforcing member and said distal portion of said register member flex into said second flexure-receiving enlargement and make liquid-tight contact with the catheter; and
   (g) when no catheter is received in said hemostasis valve, said reinforcing member provides a liquid-tight seal of said first bore.

2. A hemostasis valve as recited in claim 1 and further comprising a fourth bore located in said main body and extending from a surface of said main body to said first bore.

3. A hemostasis valve as recited in claim 1 wherein said proximal end cap is permanently fixed to said main body.

4. A hemostasis valve as recited in claim 1 wherein said proximal end cap is cup-shaped.

5. A hemostasis valve as recited in claim 4 wherein said proximal portion of said register member makes planar abutting contact with said proximal end cap at a surface at least approximately perpendicular to said third bore.

6. A hemostasis valve as recited in claim 1 wherein said reinforcing member makes planar abutting contact with the distal portion of said register member at a surface at least approximately perpendicular to said third bore.

7. A hemostasis valve as recited in claim 1 wherein said at least one slit in said reinforcing member is a tricusp slit.

8. A hemostasis valve as recited in claim 1 wherein said first flexure-receiving enlargement is much longer in the direction of said first bore than is necessary to receive the flexure of said reinforcing member.

9. A hemostasis valve as recited in claim 1 and further comprising a reinforcing ring located between said reinforcing member and said register member.

10. A hemostasis valve as recited in claim 9 wherein said register member, said reinforcing ring, and said reinforcing member are permanently joined into a subassembly.

11. A hemostasis valve as recited in claim 1 wherein said register member ad said reinforcing member are permanently joined into a subassembly.

12. A hemostasis valve as recited in claim 1 wherein the transverse dimension of said third bore are smaller than the transverse dimensions of the catheter that, in use, is to be passed through the hemostasis valve.

13. A hemostasis valve as recited in claim 1 and further comprising a hang-up hole extending through said main body.

14. A hemostasis valve as recited in claim 13 wherein said hang-up hole is at least approximately perpendicular to said first bore.

* * * * *